United States Patent [19]

Schneider et al.

[11] Patent Number: 4,490,016
[45] Date of Patent: Dec. 25, 1984

[54] POLARIMETRIC IMAGE RECORDER

[75] Inventors: Irwin Schneider, Alexandria, Va.; Charles S. Guenzer, Washington, D.C.

[73] Assignee: The United States of America as represented by the Secretary of the Navy, Washington, D.C.

[21] Appl. No.: 395,431

[22] Filed: Jul. 6, 1982

[51] Int. Cl.³ .................. G02B 5/30; G02B 27/18; G11C 13/04
[52] U.S. Cl. ................................. 350/397; 365/119
[58] Field of Search ............... 350/354, 370, 396–398, 350/3.61, 3.64; 365/119, 121

[56] References Cited

U.S. PATENT DOCUMENTS

| | | | |
|---|---|---|---|
| 3,466,616 | 9/1969 | Bron et al. | 365/119 |
| 3,727,194 | 4/1973 | Schneider | 365/119 |
| 3,771,150 | 11/1973 | Schneider | 365/119 |
| 3,934,234 | 1/1976 | Burt | 365/119 |
| 4,038,647 | 7/1977 | Schneider | 365/119 |

OTHER PUBLICATIONS

Schneider et al., "Extinction Technique For Optical Storage Using Anisotropic Color Centers in Alkali Halides", App. Phys. Lett., 7–1974, pp. 77–79.

Cassasent et al., "Combined Suppressive Extinction Writing Using M & MA Centers in Li-Doped NAF", App. Phys. Lett., 11–1976, pp. 660–662.

Shono et al., "Image Recording on $F_A$ Centered Crystals by He-Ne Laser", Appl. Phys. Lett., 3–1973, pp. 299–300.

Primary Examiner—William H. Punter
Attorney, Agent, or Firm—Robert F. Beers; William T. Ellis; Charles S. Guenzer

[57] ABSTRACT

A polarimetric image recorder which records only the net polarization of the viewed scene. An optical lens system projects the light originating from the viewed scene onto a thin layer of an alkali halide crystal containing anisotropic color centers. Polarized light reorients the color centers and creates a net polarization in the layer. The net polarization of the layer is read by such means as shining polarized light through the layer and then through a polarizer set perpendicularly to the polarization of the light source. Whatever light is viewed through the reader represents a net polarization in the scene.

12 Claims, 7 Drawing Figures

POLARIMETRIC IMAGE RECORDER

BACKGROUND OF THE INVENTION

The invention relates, in general, to an optical system for recording an image of a scene and in particular to an image recorder that utilizes anisotropic color centers to record only the net polarization of light emanating from the scene.

Description of the Prior Art

In various fields of remote sensing, the image of a scene, as presented in ordinary light, does not clearly reveal the desired structure of the scene. In many instances, the image of the desired structure is intensified, i.e., presented in higher contrast, if the polarization of the light in the image of the scene is taken into account. A polarimetric image recorder should detect only the net linear polarization of a scene and not record light that is randomly polarized or circularly polarized. If a part of a scene emits equal amounts of light linearly polarized in perpendicular directions, the two perpendicular polarizations cancel and are not recorded. Polarimetric image recording is useful in meterology and atmospheric science for distinguishing hazy forms, in water pollution monitoring for detecting thin surface layers, in geological and archaeological prospecting for distinguishing small surface variations, and in medical diagnosis and forensic medicine for distinguishing cellular variations.

The presence of polarized light can be detected by viewing the scene through a rotatable polarizer and noting in which part of the scene the image changes as the axis of polarization changes. Such detection is simple but subjective and lacks a record of the image.

A more analytical method utilizes a photographic process, wherein the scene is recorded twice through polarizers set at right angles for the two photographs. Each of the photographic images containing all of the light of the set polarization is recorded on its own negative. The developed negatives can then be compared visually or with a densitometer to note any difference between them. This method requires the development of photographic film and then a point-by-point comparison of the two images to detect any differences. If the scene is composed mostly of unpolarized light with only a small fraction of the light in any portion of the scene being preferentially polarized, then only small differences in the two images will occur. Since granularity and non-uniformity in the film introduce noise in the image, a small difference in the two images may be indistinguishable from the noise. Such a limitation imposed by finite resolution and a large background is called the dynamic range of the system.

Another approach avoids the processing and interpretation delays associated with photographic film by the use of two television cameras with mutually perpendicular polarizers in front of the two lenses each passing different polarizations of light. Halajian et al. (U.S. Pat. No. 3,864,513) describe a polarimetric image detector wherein the two polarized images are separately digitized point-by-point and the resulting digital data are stored in separate memory locations. Subsequent digital processing would reveal any differences of the images. The dynamic range of this approach is limited by the dynamic range of the television cameras as well as the digitization noise inherent in a finite-sized digital word, so that a small net polarization cannot be extracted from a bright scene.

Garlick et al. (U.S. Pat. No. 3,992,571) describe a different television system wherein the two video signals arising from the differently polarized images are compared over the whole scene on a point-by-point basis by an analog circuit, the output of which is a ratio of the difference to the sum of the two signals. The differenced output signal is then displayed on a cathode ray tube. Smart (U.K. Pat. No. 1,149,064) compares a polarized image with an unpolarized image in a television system. These real time systems are limited by the dynamic range of the television cameras and the difference amplifier. Furthermore, any system relying on two television cameras, a cathode ray tube and high speed analog electronics will be bulky and have potential reliability problems.

Anisotropic color centers present a potential method for recording an image composed of polarized light. The use of anisotropic color centers for information storage was described by Bron in U.S. Pat. No. 3,466,616. Other techniques and systems devised for the storage and retrieval of information based on anisotropic color centers have been described by one of the present inventors in U.S. Pat. No. 3,673,578, U.S. Pat. No. 3,720,926, U.S. Pat. No. 3,727,194, U.S. Pat. No. 3,771,150 and U.S. Pat. No. 3,846,764. These inventions all rely on the polarization induced in the recording medium by a source of light polarized along a set axis.

One of the present inventors in U.S. Pat. No. 4,038,647 used anisotropic color centers in a holographic recording system to initially record the joint irradiation of two waves polarized along the same axis and then to subsequently record the individual irradiations of the two waves. During the individual irradiations, the waves were polarized at a right angle to the waves of the joint irradiation so that the effects of the individual waves were subtracted out.

SUMMARY OF THE INVENTION

Therefore, one of the objects of this invention is to provide an image capable of displaying the structural detail of a scene.

Another object of this invention is to provide an image recorder sensitive only to the net linear polarization of a scene.

A further object of this invention is to provide a polarimetric image recorder with a large dynamic range in the total light intensity.

Yet another object of this invention is to provide a polarimetric image recorder which can be read in real time.

The polarimetric image recorder of the present invention relies upon anisotropic color centers in a medium which reorient when exposed to electromagnetic radiation of a given wavelength that is polarized relative to the electric dipole moment of the color center. A layer of the medium is exposed to both polarizations of the light originating from the scene and of a wavelength to which the color centers are sensitive. Light polarized along a possible color center orientation will affect the population with that orientation. The resulting population of the color centers will reflect the net polarization of the light falling on that area of the layer containing the color centers. An image of the polarization of the layer is an image of the net polarization of the scene.

The invention described here improves over the prior art in several respects. Use of a recording medium allows an objective recording of polarimetric images. The recording of the image with color centers is simple and requires no chemical processing nor complex electronics. Only a single imaging system and a single recording system are required. The dynamic range of the technique can be much greater than with dual recording media. However, the technique is sensitive to only part of the visible spectrum. Furthermore, the recording efficiency of color centers is consideraby less than that of film or television cameras.

The present invention relies on physical principles similar to those used in the holographic recording system of a co-inventor's U.S. Pat. No. 4,038,647 but uses a different apparatus to record two functionally similar but independent and mutually perpendicularly polarized irradiations in order to record a net polarization rather than three separate irradiations of different types. The present invention also differs from the co-inventor's other patents for information storage by color centers in that an unknown combination of polarizations is recorded rather than an exposure by a set polarization. Furthermore in the inventions of these other patents, the only image reversal was done in the erasure step by a heavy irradiation of unpolarized light.

These and other objects, advantages and novel features of the invention will become apparent from the detailed description of the invention when considered in conjunction with the accompanying drawings.

DETAILED DESCRIPTION OF THE INVENTION

Figure 1:
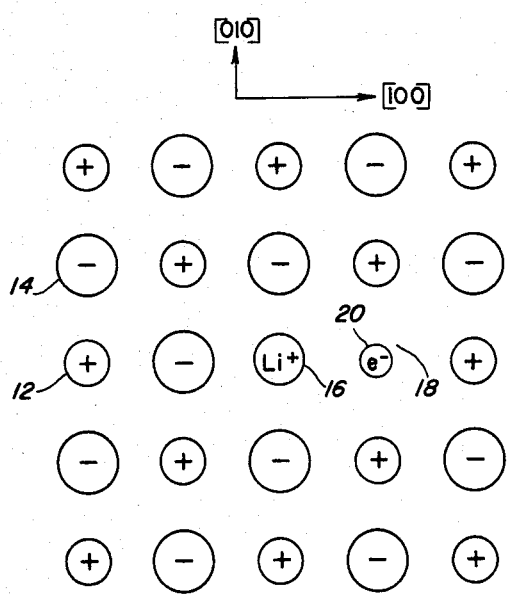
FIG. 1 is a plane view of a lithium $F_A$ color center in a crystal.

The invention depends upon the interaction of polarized light with anisotropic color centers in materials such as alkali halides. The crystal structure of such a material is shown in FIG. 1. For this example, an $F_A$ center of lithium (Li) in potassium chloride (KCl), of the type discussed in the co-inventor's U.S. Pat. No. 3,673,578, will be shown but it is to be understood that the invention is not limited to such a combination but can be used with any material having anisotropic color centers that reorient in the presence of polarized light.

The host alkali halide lattice shown in FIG. 1 is composed of positively charged alkali ions 12 potassium in this case, and negatively charged halide ions 14, chlorine in this case, which are arranged in a regular alternating square pattern on the (001) crystalline face characteristic of the face-centered cubic crystal. A view of the crystal structure along any other cubic direction will present the same regular structure. A lithium $F_A$ color center occurs when a lithium ion 16 replaces the host alkali ion in the lattice with a halide vacancy 18 as a nearest neighbor. The halide vacancy 18 contains one trapped negatively charged electron 20. The presence of the positively charged lithium impurity 16 results in an electric dipole along the [100] direction for the configuration shown. The $F_A$ color center is anisotropic because it has a lower symmetry than the cubic alkali halide host lattice. Three fully equivalent $F_A$ color centers could exist, depending on whether the vacancy-impurity axis lies along [100] as shown in FIG. 1, or along [010] or [001]. Light can interact with and be absorbed by an $F_A$ center provided the light has a finite component of electric field along the electric dipole moment of that color center.

Figure 2:
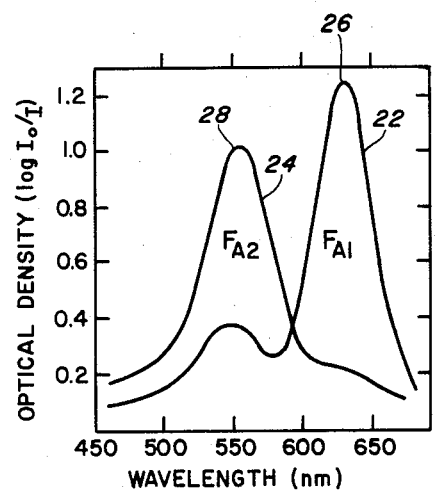
FIG. 2 is a graph plotting the dichroic absorption of light as a function of wavelength for an $F_A$ color center.

FIG. 2 illustrates the dependence on wavelength of the absorption of polarized light propagating along [001] by lithium $F_A$ color centers in potassium chloride with the $F_A$ centers mostly aligned along the [100] direction. The curves were given by R. L. Mieher in Physical Review Letters, volume 8, pages 362, 1962. One curve 22 represents the absorption of light polarized in the [100] direction. The other curve 24 is the absorption of light polarized in the [010] direction. The [100] curve 22 has an absorption called the $F_{A1}$ band which has a peak 26 at around 629 nm. The [010] curve 104 shows the $F_{A2}$ transition which peaks 28 at around 533 nm. The absorption spectrum for unpolarized light would be an average of the two curves 22 and 24, The $F_{A1}$ peak represents the transition for a quantum mechanical p-state with its dipole moment aligned parallel to the vacancy-impurity axis of the color center while the $F_{A2}$ peak represents the two p-transitions with dipole moments transverse to the vacancy-impurity axis.

If a material's absorption of light depends on the polarization of the light relative to the material, the material is dichroic. Any dichroic material is also birefringent, i.e., the index of refraction differs for different polarizations of light. As a result a dichroic material will change the polarization of light passing through it. The transmitted intensity is equal to the sum of an absorptive or dichroic component which rotates the plane of polarization of the passing light and the dispersive or birefringent component which in general converts incoming linearly polarized light into elliptically polarized light. Suitable recording materials for this invention must be such that the materials will record an image using dichroism or birefringence induced in them by realigning the anisotropic color centers with polarized light.

Figure 3:
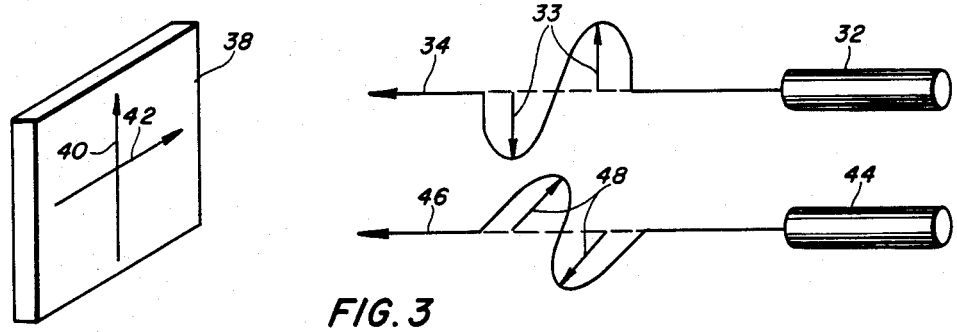
FIG. 3 is a schematic of the interaction of polarized light with anisotropic color centers.

FIG. 3 shows the physical mechanisms underlying this invention, in which a light source 32 emits a beam of light the electric field 33 of which is confined to one plane, in this case oriented in the vertical direction. The light 34 is directed onto a layer of an alkali halide medium 38 containing color centers some of which are oriented vertically 40, others of which are oriented horizontally 42. If the light 34 is of a wavelength corresponding to the $F_{A1}$ transition, then only the vertically oriented color centers 40 will interact with the vertically polarized light 34. Conversely, if the light 34 is of wavelength $F_{A2}$, the vertically polarized light 34 will interact with the horizontally oriented color centers 42 as well as centers oriented perpendicular to the plane of FIG. 1, i.e., along the direction of propagation of the light 34.

Both of these allowed transitions when excited will cause the color centers to reorient, at least on the average. The interaction puts the color center into an excited state from which it can relax into a different orientation, possibly an orientation that will no longer interact with the polarized light of that wavelength. Upon continued polarized irradiation, the population of color centers with an orientation that allows an interaction will decrease, while the population of other orientations not allowing an interaction will increase.

Vertically polarized $F_{A1}$ light 34 in FIG. 3 will decrease the population of vertically oriented color centers 40 while increasing the number of horizontally oriented color centers 42. Similarly a light source 44 producing $F_{A1}$ light 46 the electric field 48 of which is horizontally polarized will decrease the number of horizontally oriented color centers 42, but increase the vertical color centers 40, since horizontally polarized light 46 excites the same color centers as vertically polarized light 36.

The final populations of vertical 40 and horizontal 42 color centers depends on the relative intensities of the two polarized light sources 32 and 44. If the two sources 32 and 44 are of equal intensity, then the populations of color centers oriented along the two directions 40 and 42 will be equal after the exposures if they were equal before. However, if the two beams are of unequal intensity, e.g., the vertically polarized light beam 34 is slightly more intense than the horizontally polarized beam 46, more centers will be oriented along the horizontal direction 42 than the vertical direction 40 and the alkali halide layer becomes slightly dichroic or birefringent. Unpolarized light does not record; only light with a net linear polarization records.

Light of wavelength $F_{A2}$ can be used in the same procedure to record a net linear polarization and it offers the advantage over $F_{A1}$ light that it interacts with color centers oriented parallel to the light's propagation. This interaction avoids a problem with $F_{A1}$ light which excites only color centers aligned perpendicular to the direction of propagation of light. These centers can relax into color centers aligned parallel to this direction which thereafter cannot be excited by light of either polarization, i.e., $F_{A1}$ light bleaches the alkali halide by driving the color centers into an alignment parallel to the propagation of light with a resultant loss of sensitivity.

Up to this point, the light beams 34 and 46 have been assumed to be uniform over their cross sections. However, if the beams contain an image, the intensity of the beam will vary over the area of the alkali halide layer 38, but the same mechanisms will occur at each point of the image. As a result, a net polarization image of the images represented by the two beams 34 and 46 will be recorded in the alkali halide layer 38.

Figure 4:
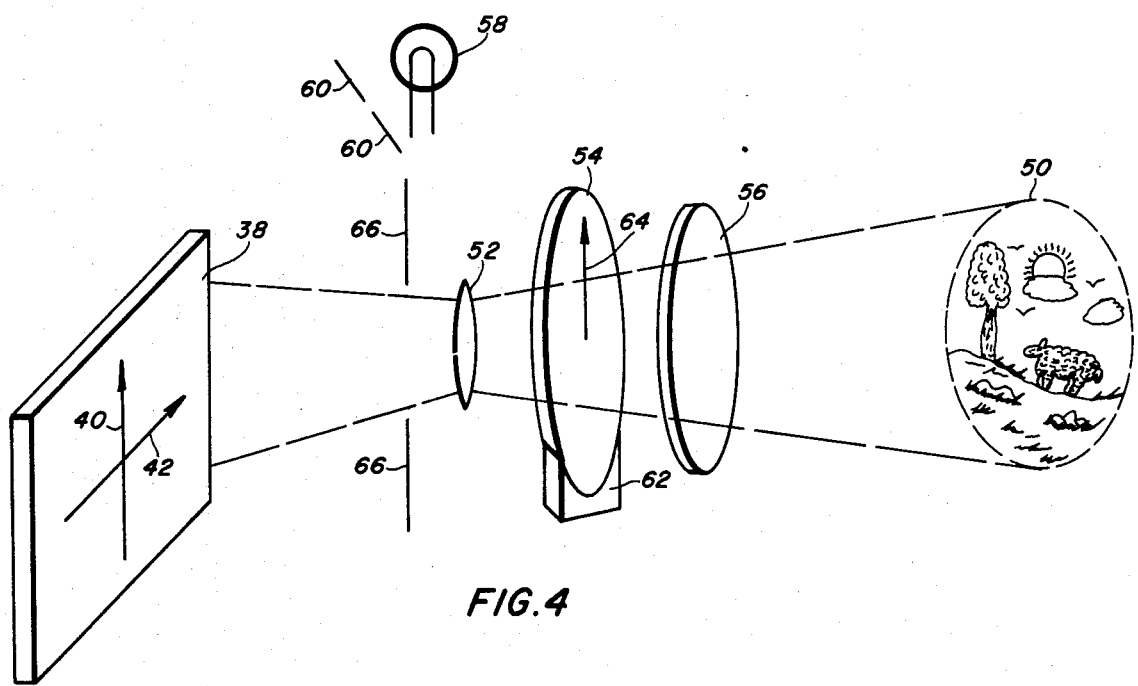
FIG. 4 is a schematic of the invention using a rotatable polarizer.
Figure 5:
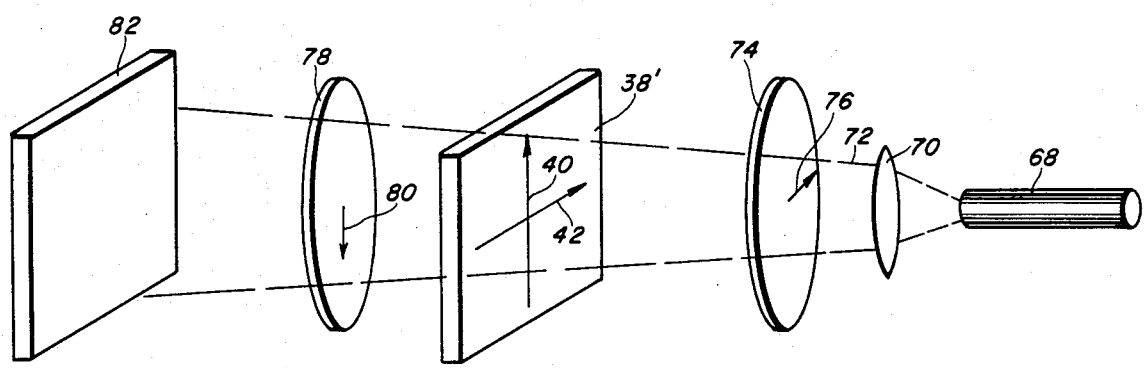
FIG. 5 is a schematic of an apparatus for reading an exposed sheet.

The invention is an optical system for recording an image of a scene such that only the net polarization of light originating from the scene is recorded. FIG. 4 shows a system which would accomplish this object. The scene 50 is imaged upon the alkali halide layer 38 by means of an optical lens system 52 here represented by a single lens. Not shown is a light-tight box surrounding the alkali halide layer 38 to prevent extraneous light from reaching the alkali halide. Also not shown are the cooling means that may be necessary to maintain the alkali halide at a temperature low enough so as to prevent thermal reorientation of the color centers. For lithium $F_A$ centers in potassium chloride, the temperature must be maintained below $-65°$ C. The embodiment shown in FIG. 4 includes a rotatable polarizer 54, a color filter 56 and a light source 58 for initial randomizing. The apparatus for reading of the polarization induced in the alkali halide layer 38 is shown in FIG. 5.

With reference again to FIG. 4, the populations of vertical 40 and horizontal 42 color centers are intially equalized by a heavy irradiation from a source 58 of unpolarized $F_{A2}$ light such as a light bulb controlled by a set of shutters 60. Alternately, a polarized laser with its axis of polarization set at 45° between the color center directions 40 and 42 will randomize the populations. Continued annealing at high temperatures will also randomize the color centers. A color filter 56 can be placed in the beam to eliminate the competing effect of the $F_{A2}$ light. Such a filter would have an absorption edge between $F_{A1}$ and $F_{A2}$ or be an interference filter for $F_{A2}$. If $F_{A2}$ light is being used, the color filter should eliminate $F_{A1}$ light. The axis of polarization 64 of the polarizer is initially set vertically.

A polarimetric image can be recorded in an alkali halide by a double exposure technique. This involves a first exposure of the alkali halide layer or medium 38 made by opening the main shutter 66 in the light-tight box for a fixed time. After completion of the first exposure, the axis of polarization 64 of the polarizer is rotated 90° to lie horizontally. Then a second exposure of the same duration as the first is made as soon as possible after the first in order to minimize any temporal change in the scene 50.

After the dual exposures, the alkali halide layer 38 contains the polarimetric image. Any method which can read the spatial variation of the net polarization induced in the alkali halide layer 38 will be reading the net polarized image originating from the scene 50. One such method shown in FIG. 5 requires that the alkali halide layer containing the color centers be in the form of a flat platelet or sheet 38'. A source of light 68 provides visible light of a wavelength which the color centers in the alkali halide are relatively insensitive to reorientation but nonetheless still produce birefringence when there is a net polarization. For $F_A$ centers in KCl such light would have wavelengths greater than 650 nm. A laser could be used but coherent monochromatic light is not required. A lens system 70 provides a uniform collimated optical beam 72. A first polarizer 74 with its axis of polarization 76 set at a fixed angle is placed between the light source 68 and the exposed alkali halide sheet 38'. If a laser which emits a linearly polarized beam is used as the light source 68 the first polarizer is unnecessary. On the other side of the alkali halide sheet 38' is placed a second polarizer 78 with its polarization axis 80 set at 90° to the polarization axis 76 of the first polarizer 74 or the laser. The beam finally falls upon the viewer 82 which is optically sensitive to the light emitted from the source 68. The viewer may be an optical ground glass, a piece of photographic film, a photosensitive electronic array such as a vidicon or other types of optical viewers.

If the alkali halide sheet 38' is unpolarized, then no light reaches the viewer 82 which thus remains dark because the first polarizer 74 transmits light of a polarization which the second polarizer 78 blocks. However, the parts of the alkali halide sheet 38' that have a net polarization, due to an imbalance of vertical 40 and horizontal 42 color centers, will cause the polarization of the dichroic component of the light passed by the first polarizer 74 to rotate. Whatever polarized light has been rotated in the sheet 38' will pass at least partially through the second polarizer 78 and thus illuminate that part of the viewer 82. The larger the net polarization in the alkali halide sheet 38', the greater the amount of light transmitted through the second polarizer 78 and the more light which illuminates the viewer 82. The result is that the viewer 80 displays only the net polarization of the scene 50.

The reader shown in FIG. 5 has been described as a separate apparatus but it could be incorporated into the same light-tight box as the image recorder shown in FIG. 4, so that the alkali halide sheet 38' need not be moved between the steps of recording and reading.

Figure 6:
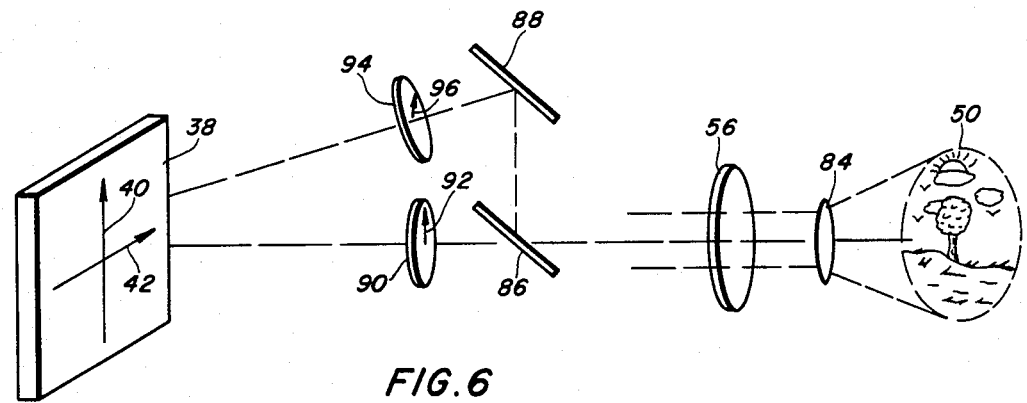
FIG. 6 is a schematic of the invention using a partially transmitting mirror.

Alternative recording configurations than that described for FIG. 4 offer the advantage of requiring only one exposure. Shown in FIG. 6 is a recording configuration which splits the beam. The scene 50 is optically imaged by a lens system 84 into a beam which passes through a color filter 56 which absorbs $F_{A2}$ light. A half-silvered mirror 86 or beam splitting prism splits the beam so that half of it transmits to the alkali halide layer 38. The other half is reflected by a high reflectivity second mirror 88, aligned so that the beams again register on the alkali halide layer 38. A first polarizer 90 has its axis of polarization 92 set vertically. A second polarizer 94 is set in the reflected beam with its plane of polarization 96 set horizontally.

The shutters, light-tight box, cooling equipment, initial randomizing illuminator and reading equipment described in FIGS. 4 and 5 would be required as well for the configuration of FIG. 6.

The result is a simultaneous exposure of the alkali halide layer 38 by both polarizations. Any temporal variations in the scene 50 would be felt in the exposures of both polarizations.

The simultaneous exposure has the advantage of extending the dynamic range of the alkali halide layer 38. The number of color centers reoriented by one polarization of light cannot exceed the number of color centers if the recording is done by separate exposures. This limitation holds for the separate exposure procedure even if the two polarizations of light differ only slightly in intensity so that only a few of the color centers would be finally reoriented absent the limitations. However, if the two polarization exposures are done simultaneously there is a continuing interchange between the two orientations of color centers 40 and 42. The dynamic range in a simultaneous exposure is controlled by the difference of the two polarized light sources, rather than by the greater of the two.

A simultaneous recording configuration allows the possibility of reading the recorded image simultaneously as it is being recorded as long as the reading light is at a sufficiently different wavelength from $F_{A1}$ so that it does not significantly reorient the color centers during reading.

Figure 7:
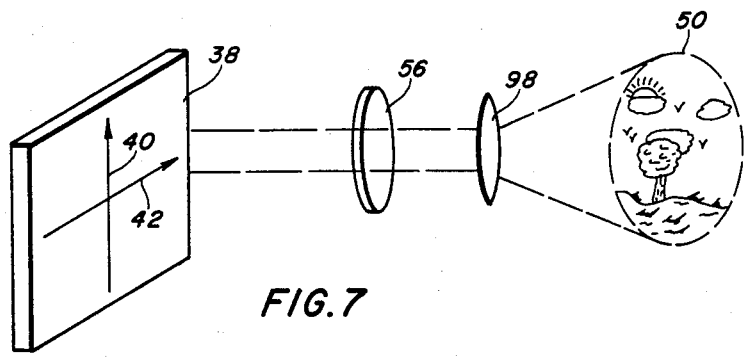
FIG. 7 is a schematic of the invention requiring one exposure with one beam.

Another simultaneous recording configuration is shown in FIG. 7 which does not require the use of polarizers or beam splitters. The scene 50 is imaged by a lens system 98 through a color filter 56 absorbing the $F_{A2}$ radiation (or absorbing $F_{A1}$ if $F_{A2}$ is being recorded). Thereafter the light falls upon the alkali halide layer 38 containing the two orientations of color centers 40 and 42. Also required are the shutters, light-tight box, cooling equipment, means for initially randomizing the orientation of color centers and reading equipment. These have been adequately described for the other configurations and their use here is completely analogous.

An understanding of the simple configuration of FIG. 7 as being equivalent to the configuration of FIG. 6 requires an understanding of the interaction of the light with the color center's dipole in the context of quantum mechanics. The interaction is a single photon interaction between the color center's dipole moment $|p>$ and the photon $|a>$ so the interaction term is $<p|W|a>$, where W is the interaction potential. Let the dipole be that of the vertically oriented color centers $|p_v>$. The light photon can be represented as a linear combination of horizontally and vertically polarized photon wave functions $$|a> = a_v|V> + a_h|H>. \tag{1}$$

The relative values of the coefficients $a_v$ and $a_h$ determine the polarization of the photon $|a>$. If $a_h$ is zero then $|a>$ is vertically polarized; a zero value for $a_v$ implies a horizontal polarization. In the more general case, neither $a_v$ nor $a_h$ are zero. An unpolarized beam of light contains many photons which have coefficients varying from photon to photon. The values of the coefficients of the photon wave functions are determined by the process creating the photon and subsequent interactions with reflectors, polarizers and the like.

The interaction term can be rewritten as $$<p_v|W|a> = a_v<p_v|W|V> + a_n<p_v|W|H> \tag{2}$$

Since there is no interaction between a vertically oriented color center 30 and horizontally polarized light for $F_{A1}$ interactions, the last term must be zero so that $$<p_v|W|a> = a_v<p_v|W|V> \tag{3}$$

The similar interaction term for the horizontal color center $|p_h>$ is given by $$<p_h|W|a> = a_h<p_h|W|H> \tag{4}$$

By symmetry arguments for a cubic crystal, the right hand terms in the two last equations are equal to a constant independent of the particular photon or the orientation of the dipole. In quantum mechanical language, the probability of a vertical color center reorienting is proportional to $a_v^2$; likewise, the probability of a horizontal color center relocating is proportional to $a_h^2$. It is not required that the photons impinging on the alkali layer 38 be polarized completely in the vertical or horizontal direction by the use of polarizers 54, 90 or 94. The final populations of color centers will be dictated by the wave function coefficients. These same probabilities will obtain if transmission of light through a polarizer is rigorously derived.

The configuration shown in FIG. 7 accomplishes the same result with fewer parts than that in FIG. 6. It also requires half the exposure and has much reduced alignment requirements.

Color centers of types other than the $F_A$ center in KCl can be used in this invention. Other anisotropic color centers in KCl are used for information storage in one of to co-inventor's U.S. Pat. Nos. 3,727,194, 3,771,150 and 3,846,764. He and other co-inventors describe the fabrication of various alkali fluoride crystals with color centers suitable for this invention in U.S. Pat. No. 4,087,374. Yet other types of anisotropic color centers can also be used if they reorient in the presence of polarized light. Anisotropic color centers that behave in this manner include sodium $F_A$ centers, $F_2$ centers (previously called M) and $(F_2)_A$ centers (previously called $M_A$). Other possible host crystals include most of the alkali halides, e.g. KCl, KF, KBr, KI, NaCl, NaF, LiF, RbCl and RbBr. Other ionic crystals such as the alkaline earth fluorides can be used although their non-cubic crystal structure introduces complications.

What has been described is a polarimetric image recorder operating in real-time for recording only the net polarization of light emanating from a scene.

Obviously many modifications and variations of the present invention are possible in light of the above teachings. It is therefore to be understood that within the scope of the appended claims, the invention may be practiced otherwise than as specifically described.

What is claimed and desired to be secured by Letters Patent of the United States is:

1. A polarimetric image recorder of a scene, comprising:
   a layer of alkali halide material containing anisotropic color centers exhibiting photoinduced birefringence;
   means for imaging two polarizations of light from the scene upon said layer, each said polarization exciting the same color centers in said layer; and
   means for reading the polarization induced in said layer by said light.

2. A polarmetric image recorder as recited in claim 1, further comprising:
   a polarizer disposed between said scene and said layer; and
   means for rotating the polarization axis of said polarizer by 90°.

3. A polarimetric image recorder as recited in claim 1, further comprising:
   means for dividing the beam of said light imaged upon said layer into two separate beams; and
   two polarizers intercepting said separate beams with their polarization axes set at 90° to each other.

4. A polarimetric image recorder as recited in claim 3 wherein the light from the scene is divided into two beams by a partially transmitting mirror.

5. A polarimetric image recorder of a scene as recited in claims 1, 2, or 3, wherein the means for reading the polarization comprises:
   a beam of polarized light aligned to shine through said layer and of a wavelength at which the alkali halide material can be birefringent but less efficient at reorienting the color centers than the light from the scene;
   a polarizer intercepting said beam after it passes through said layer, the polarization axis of said polarizer being at 90° to that of said beam; and
   an optical viewer for said beam positioned to intercept said beam after it passes through said polarizer.

6. A polarization imager as recited in claim 1, 2, or 3 wherein said alkali halide material is potassium chloride and said color center is $F_A$.

7. A polarization image recorder as recited in claim 1, 2, or 3, further comprising a color filter disposed between said scene and said layer.

8. A method for recording a polarized scene, comprising the steps of:
   imaging simultaneously both polarizations of light from said scene upon a layer of alkali halide material containing anisotropic color centers exhibiting photoinduced birefringence; and
   reading the net polarization induced in the layer by the light.

9. A method for recording a polarized scene, comprising the steps of:
   imaging the light from the scene through a polarizer upon a layer of alkali halide material containing anisotropic color centers exhibiting photoinduced birefringence; then
   rotating the polarization axis of the polarizer by 90°; then
   imaging the light from the scene through said polarizer upon said layer for the same exposure as first imaging step; and
   reading the net polarization induced in said layer by the light.

10. A method for recording a polarized scene, comprising the steps of:
    imaging the scene in two beams;
    directing said beams through separate polarizers with their polarization axes set at a right angle to each other;
    projecting said beams, with the images therein aligned, onto a layer of alkali halide material containing anisotropic color centers exhibiting photoinduced birefringence; and
    reading the polarization induced in said layer by the two beams.

11. A method for recording a polarized scene as recited in claim 8, 9, or 10, wherein said material is potassium chloride and said color ceneter is $F_A$.

12. A method for recording a polarized scene as recited in claim 8, 9, or 10, further comprising filtering said light imaged upon said layer according to its wavelength.

* * * * *